United States Patent
Acha Gandarias

(10) Patent No.: US 9,629,534 B2
(45) Date of Patent: Apr. 25, 2017

(54) ILLUMINATED OPTICAL LARYNGOSCOPE

(75) Inventor: Pedro Acha Gandarias, Bormujos (ES)

(73) Assignee: PRODOL MEDITEC, S.A., Bilbao (Vizcaya) (ES)

( * ) Notice: Subject to any disclaimer, the term of this patent is extended or adjusted under 35 U.S.C. 154(b) by 200 days.

(21) Appl. No.: 14/008,437

(22) PCT Filed: Mar. 20, 2012

(86) PCT No.: PCT/ES2012/000065
§ 371 (c)(1),
(2), (4) Date: Sep. 27, 2013

(87) PCT Pub. No.: WO2012/131118
PCT Pub. Date: Oct. 4, 2012

(65) Prior Publication Data
US 2014/0018629 A1 Jan. 16, 2014

(30) Foreign Application Priority Data
Mar. 28, 2011 (ES) .................................. 201100354

(51) Int. Cl.
*A61B 1/267* (2006.01)
*A61B 1/00* (2006.01)
*A61B 1/12* (2006.01)

(52) U.S. Cl.
CPC .......... *A61B 1/267* (2013.01); *A61B 1/00135* (2013.01); *A61B 1/127* (2013.01)

(58) Field of Classification Search
CPC ............................ A61B 1/267; A61B 1/00105
USPC ................ 600/193, 196, 197, 186, 189, 199
See application file for complete search history.

(56) References Cited

U.S. PATENT DOCUMENTS

| 3,426,749 | A | * | 2/1969 | Jephcott | A61B 1/00142 |
| | | | | | 206/363 |
| 5,695,454 | A | * | 12/1997 | Mourkidou | A61B 1/2673 |
| | | | | | 600/121 |
| 5,846,183 | A | | 12/1998 | Chilcoat | |
| 6,569,089 | B1 | * | 5/2003 | Covington | A61B 1/0669 |
| | | | | | 600/199 |
| 6,843,769 | B1 | * | 1/2005 | Gandarias | A61B 1/0676 |
| | | | | | 600/185 |
| 2002/0153008 | A1 | * | 10/2002 | Schwartz | A61M 16/0488 |
| | | | | | 128/200.26 |
| 2010/0249513 | A1 | * | 9/2010 | Tydlaska | A61B 1/00052 |
| | | | | | 600/186 |

(Continued)

FOREIGN PATENT DOCUMENTS

| CN | 1371658 A | 10/2002 |
| CN | 2588931 Y | 12/2003 |

(Continued)

OTHER PUBLICATIONS

International Search Report of PCT/ES2012/000065, dated Jul. 16, 2012.

*Primary Examiner* — Eduardo C Robert
*Assistant Examiner* — Julianna N Harvey
(74) *Attorney, Agent, or Firm* — Sughrue Mion, PLLC

(57) ABSTRACT

The invention relates to an illuminated optical laryngoscope formed by an assembly, longitudinally defining a first straight segment and a second curved segment and comprising a main body (1) that is inserted into a tubular protective case (2). The curved segment of the main body (1) is formed by successive segments hinged to one another.

9 Claims, 6 Drawing Sheets

(56) References Cited

U.S. PATENT DOCUMENTS

| | | |
|---|---|---|
| 2010/0261967 A1 | 10/2010 | Pacey et al. |
| 2010/0261968 A1 | 10/2010 | Nearman et al. |
| 2011/0196204 A1* | 8/2011 | Setty .................. A61B 1/00052 600/120 |

FOREIGN PATENT DOCUMENTS

| | | |
|---|---|---|
| CN | 101810464 A | 8/2010 |
| ES | 2 160 551 A1 | 11/2001 |
| ES | 2 265 982 T3 | 3/2007 |
| WO | 96/25875 A1 | 8/1996 |
| WO | 98/19589 A1 | 5/1998 |
| WO | 2010/114621 A2 | 10/2010 |

* cited by examiner

ILLUMINATED OPTICAL LARYNGOSCOPE

CROSS REFERENCE TO RELATED APPLICATIONS

This application is a National Stage of International Application No. PCT/ES2012/000065 filed Mar. 20, 2012, claiming priority based on Spanish Patent Application No. P201100354, filed Mar. 28, 2011, the contents of all of which are incorporated herein by reference in their entirety.

TECHNICAL FIELD

The present invention relates to the practice of endotracheal interventions. It proposes a laryngoscope which allows said interventions to be practiced under advantageous conditions and with the possibility of reusing the functional device of the laryngoscope for other interventions.

PRIOR ART

The obstruction of the airway is the most frequent cause of preventable death in unconscious and traumatized patients, such that achieving permeability of the obstructed airway is thus a key issue for the recovery of individuals affected by these circumstances.

To this end, tools are used to hold the lower part of the tongue in order to clear the respiratory tract and thus be able to insert a tube which allows mechanical respiration to take place.

However, carrying out any action on the airway brings with it risks, such that in the case of unconscious and traumatized patients, the possibility of cervical injury must be taken into consideration which assumes that incorrect handling may cause severe damage.

It would, therefore, be ideal to carry out the intervention on the airway after having carried out a suitable physical examination and a radiological cervical check, however, in the majority of cases, the patient conditions necessitate immediate action, such that the intervention must be carried out by means available in situ.

Devices called laryngoscopes are available for this purpose. They are small in size and intended for orotracheal insertion; a medical professional may often carry this in their toolkit for cases of emergency.

From patent ES2160551, which has the same proprietor as the present invention, a laryngoscope is known which is formed by a tubular body comprising a straight segment and a curved end part, including an optical system of lenses and mirrors in the interior which allows observation to be carried out from one end to the other by means of said tubular body, while, at the other end of the curved part, which is blind and transparent, an illuminated point is incorporated.

Due to its shape, said laryngoscope allows for easy insertion through the mouth to the larynx; while, due to the optical and illuminated system it incorporates, it is possible to observe the interior of the larynx, thus facilitating insertion without errors.

However, during application use, the body of the laryngoscope comes into direct contact with the tissue of the patient, which, due to hygienic and sanitary conditions, renders said body of the laryngoscope unsuitable for reuse in other subsequent interventions and it must therefore be disposed of.

OBJECT OF THE INVENTION

In accordance with the invention, a laryngoscope is proposed which is designed having the constructive and functional characteristics which make it advantageous for the practice of endotracheal interventions and, which, in addition, allows the functional, constructive body of the laryngoscope per se to be reused.

The laryngoscope, which is the object of the invention, has a main body which forms the laryngoscope per se and means of protection by way of a case, the assembly defining a structure which defines a straight segment and a curved segment, with the curved segment of the main body formed by a succession of hinged segments and with the means of protection by way of a case in the form of an open tubular structure at one end and closed at the other end, wherein it is transparent, and into which case the main body may be inserted.

The main body, in its interior, includes an optical system formed by a lens provided at the rear end and a succession of mirrors and lenses longitudinally distributed along the interior part, incorporating a luminous point at the front end; while the case incorporates a tab projected towards the front in the extension of the blind end.

A laryngoscope offering the following advantages is thereby obtained:
  it anatomically adapts to the interior of the mouth and allows a visual observation of the larynx to be carried out, facilitating insertion for carrying out endotracheal interventions, as well as a visual check of the operation process during said interventions.
  It allows for orotracheal insertion into unconscious and traumatized patients, without having to force the cervical area of the patients.
  It may be quickly and easily used, without requiring specific training to use it.
  It allows for the checking and diagnosing or correction of internal anomalies in the larynx and the trachea.
  The main body constituting the laryngoscope per se may be reused, as when being inserted through the interior of the protective case, said main body does not become contaminated during application interventions, such that only the protective case must be disposed of following an application intervention of the laryngoscope.

Therefore, said laryngoscope, which is the object of the invention, emerges from a number of advantageous characteristics which give it its own purpose and preferential character for its intended function.

DETAILED DESCRIPTION OF THE INVENTION

The object of the invention relates to an illuminated optical laryngoscope consisting of a main body (1) or laryngoscope per se and external means of protection in the form of a case (2), the assembly defining a structural form comprising a rear straight segment followed by a curved segment at the front part.

Figure 1:
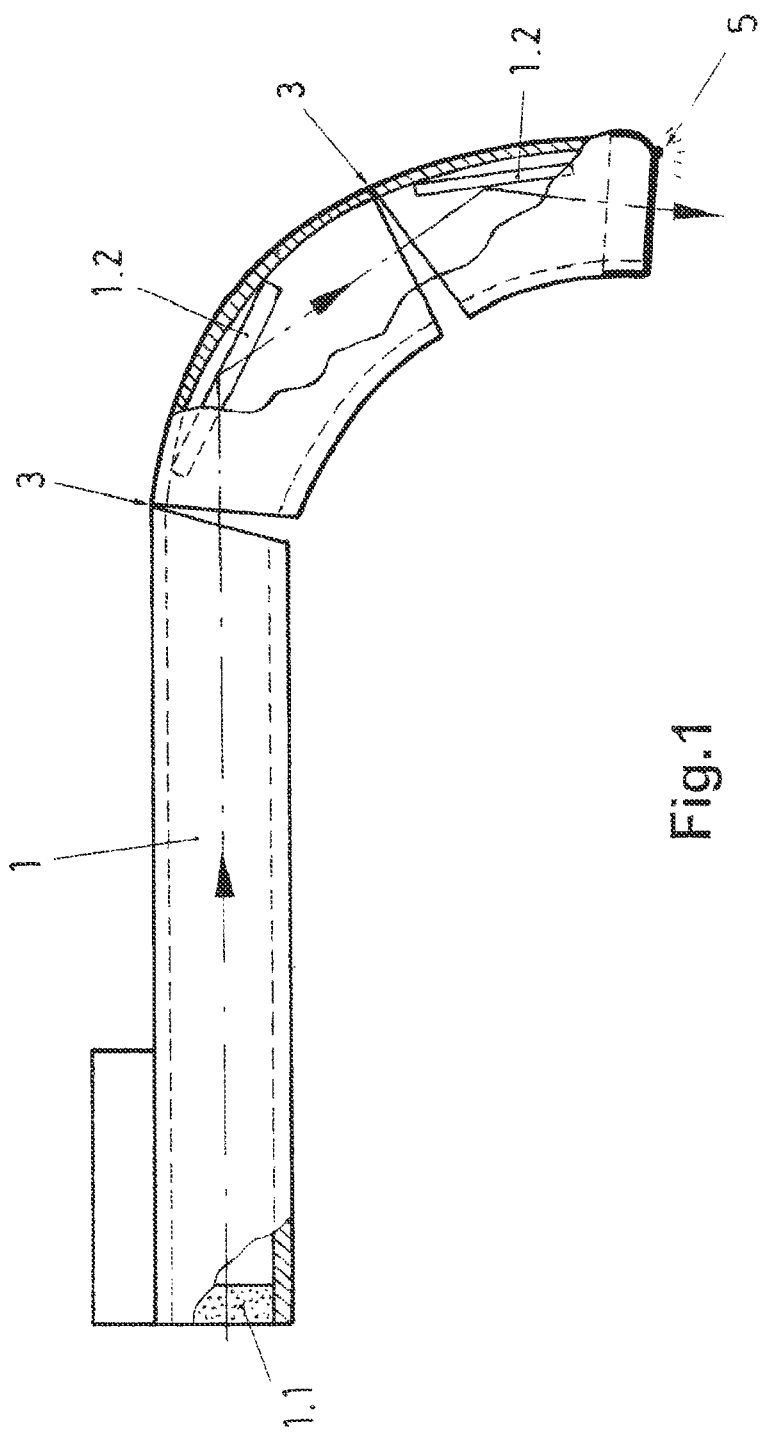
FIG. 1 shows a lateral view of the main body of the laryngoscope according to the invention, in a curved position.
Figure 6:
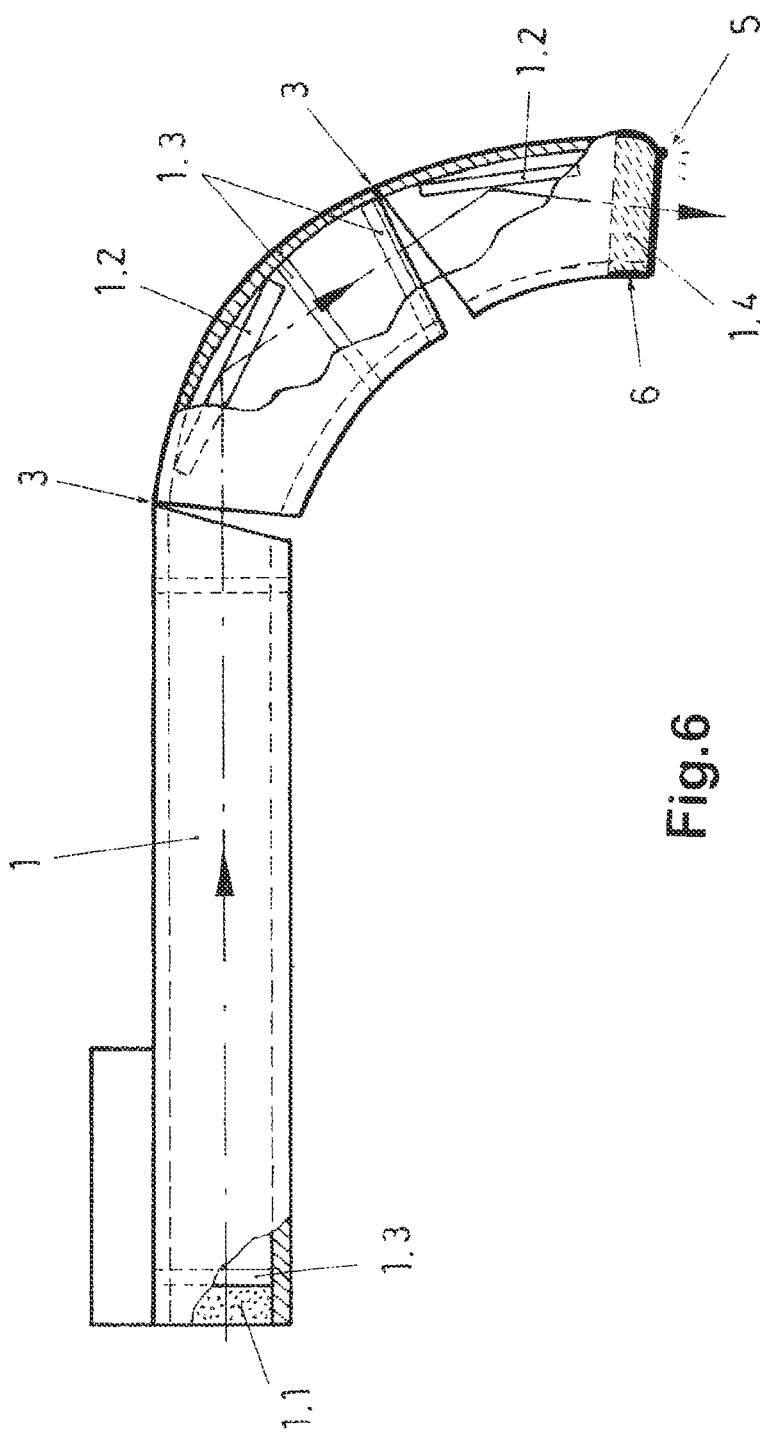
FIG. 6 is a lateral view of the main body of the laryngoscope, with another embodiment of the assembly of the optical system incorporated into the interior thereof.

The main body (1) is formed by an open tubular structure at the rear end of the straight segment and is blind at the front end of the curved segment, wherein it is transparent, incorporating an optical system allowing for visualization through the interior by means of a lens (1.1) provided at the open end and a distribution of mirrors (1.2) provided on the curved segment; while at the blind end, an illumination system is incorporated, formed by a luminous point (5) as seen in FIG. 1. An embodiment is also envisaged in which the optical system may additionally include a series of complementary lenses (1.3) distributed along the interior of the main body (1) and a prism (1.4) at the front end thereof, according to the embodiment in FIG. 6.

Figure 2:
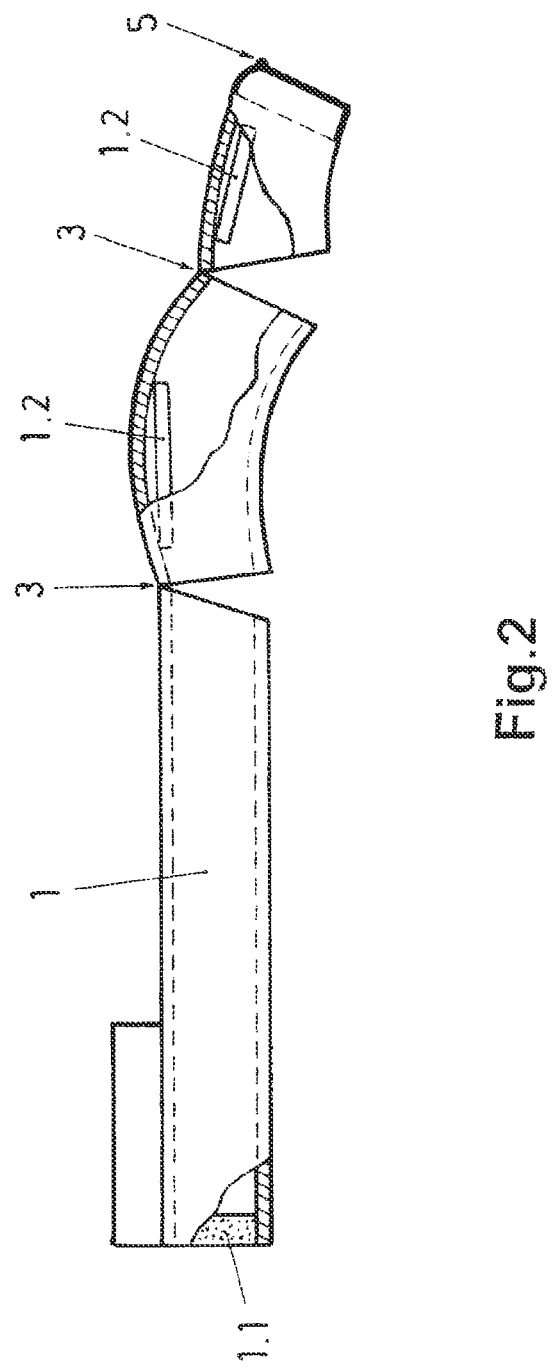
FIG. 2 is a lateral view of said main body of the laryngoscope according to the invention, in a straight position.
Figure 3:
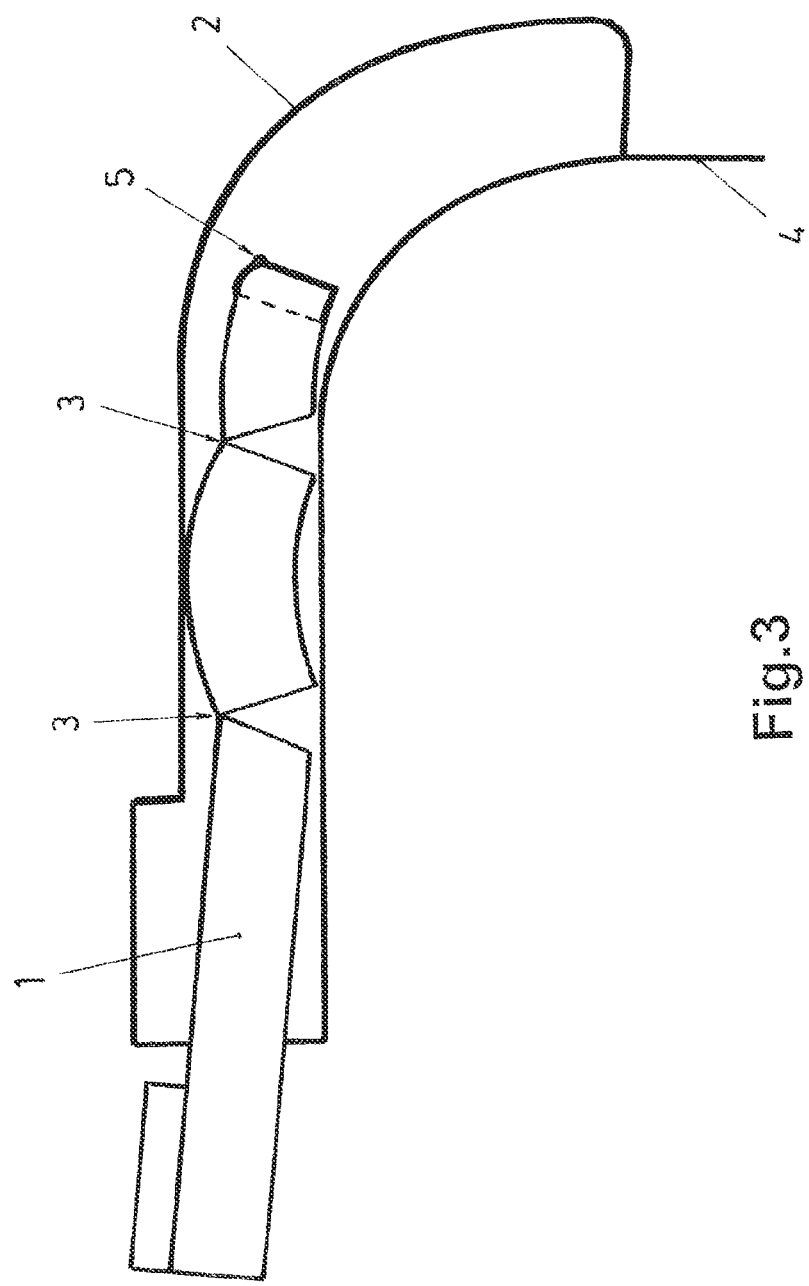
FIG. 3 shows a lateral view of the assembly of the laryngoscope, in the insertion phase of the main body into the protective case.
Figure 4:
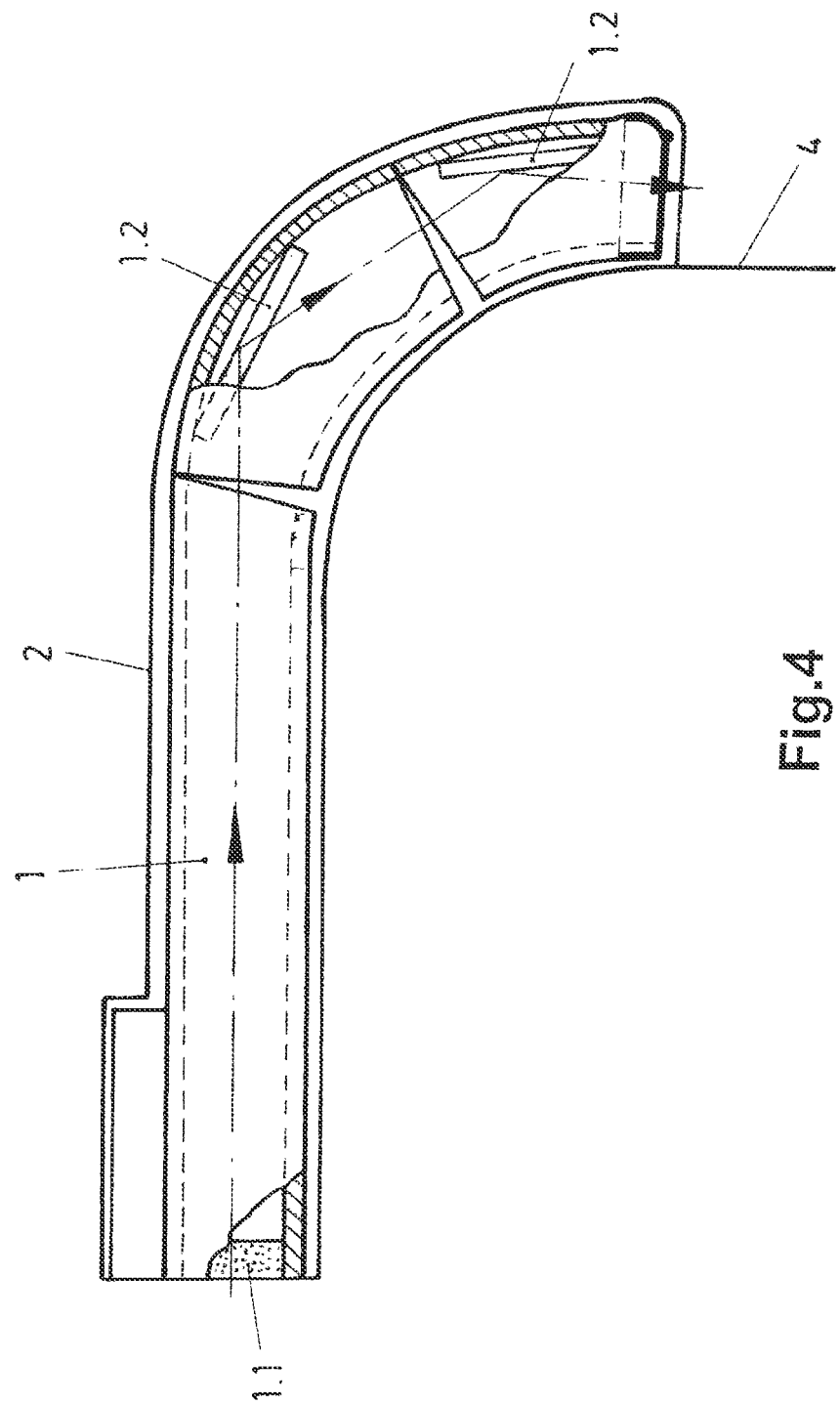
FIG. 4 is a lateral view of said assembly of the laryngoscope, with the main body housed within the protective case.

According to the invention, the main body (1) has a curve defined in a hinged manner, with a plurality of hinges (3) located on the external part of the curvature in such a way that, without affecting the inherent functionality of the laryngoscope per se, nor the function of the optical system through the interior thereof, nor the other functional aspects of the laryngoscope itself, said main body (1) may adopt a curved shape such as in FIG. 1 and a straight shape such as in FIG. 2, allowing for the insertion into the case (2) proceeding from the straight shape such that when penetrating therein, the main body (1) begins to adopt the curved shape corresponding to said case (2).

The case (2) is formed by a continuous tubular structure open at the rear end of the straight segment and blind at the front end of the curved segment, wherein it is also transparent, such that, the main body (1) may be inserted at the open rear end of said case (2), in such a way that when it is incorporated within the case, the assembly carries out the functions of a traditional laryngoscope, however with the advantage that the main body (1), which is the most expensive part of the assembly, is reusable since it remains protected by the case (2). Said main body (1) is not contaminated during application uses of the laryngoscope, with only the case (2) being disposable.

It is envisaged that the case (2) may also be formed in a hinged manner in its curved segment, in which case it includes closing means, in the form of bellows between the hinged parts in order to avoid the possibility of contaminants entering through said areas and affecting the main body (1).

At the front end of the main body (1), the provision of an anti-fogging heating system (6) is also envisaged, in order to prevent the transparent end of said main body (1) and the transparent end of the case (2) clouding up, which would make it difficult or prevent viewing the exterior of the front part of the laryngoscope through the optical system of the main body (1).

To this end, it is envisaged for the laryngoscope to be structured in such a way that the heat generated by anti-fogging system passes by diffusion in proximity to or in contact with the case (2) in order to carry out an anti-fogging function.

In addition, the case (2) itself defines a tab (4) which projects towards the front at the blind front end of said case (2), in such a way that this tab (4) facilitates the insertion of the laryngoscope via the trachea of the patient and also holds and raises the epiglottis from its lower part, thus providing a clear view of the entrance to the trachea.

Figure 5:
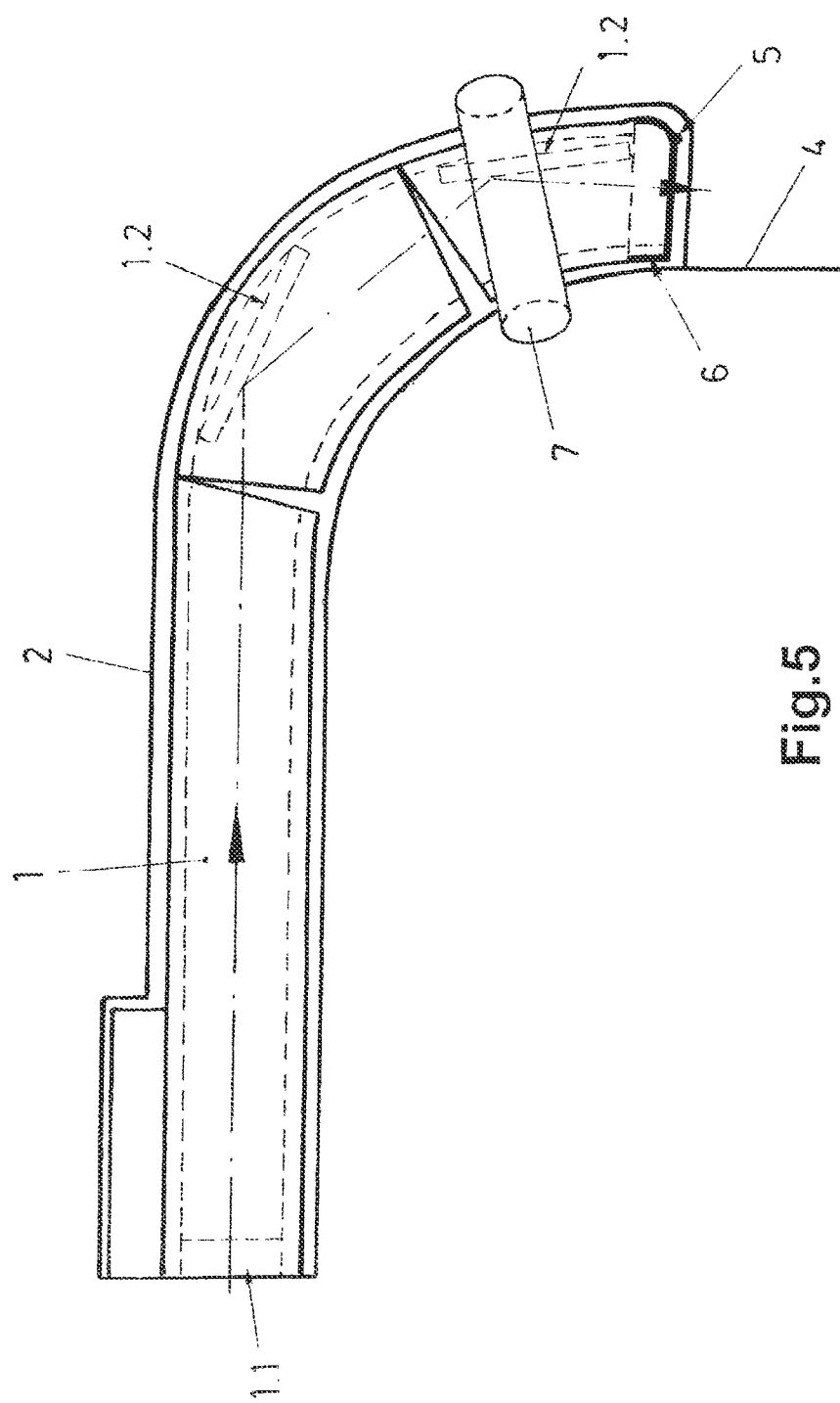
FIG. 5 is a lateral view of the assembly of the laryngoscope, with an annular body provided around the front part.

The case (2) may also be provided with a longitudinal channel for inserting an endotracheal tube; as shown in FIG. 5, a solid or inflatable annular body may also be incorporated around the front part in a sliding position on the case (2) in order to hermetically seal the airway of the patient around the laryngoscope with the aim of being able to establish endotracheal ventilation from the exterior in an effective manner. Said annular body (7) may itself define an opening in order for a tube intended for endotracheal ventilation to be passed through.

The invention claimed is:

1. An illuminated optical laryngoscope comprising: a main body formed by a tubular frame comprising a first straight segment and a second curved segment for adapting to the interior of the mouth of the patient, wherein the main body comprises an optical system in an interior of the main body and a hinge formed in the curved segment of the main body; and a case that protects the main body and that defines a tubular structure having an opening at one end and a curve shape at an opposite end and into which the main body is inserted, the second curved segment of the main body adopting the curved shape of said case when inserted.

2. The illuminated optical laryngoscope according to claim 1, wherein the curved segment of the main body comprises a succession of consecutive segments joined together by hinges on an exterior part of the curvature.

3. The illuminated optical laryngoscope according to claim 1, wherein the case comprises a tab extending from an end of the case opposite the end having the opening, the tab configured for directing insertion into the larynx of the patient.

4. The illuminated optical laryngoscope according to claim 1, wherein the case has a transparent area at an end of the case opposite the end having the opening.

5. The illuminated optical laryngoscope according to claim 1, wherein a heating system is provided between the main body and the case to prevent formation of fog on the case.

6. The illuminated optical laryngoscope according to claim 1, wherein the second segment is configured to rotate about the at least one hinge so that the second segment changes from a curved geometry to a generally straight geometry.

7. The illuminated optical laryngoscope according to claim 1, wherein the case includes the curved shape prior to being inserted into the larynx of the patient.

8. The illuminated optical laryngoscope according to claim 1, wherein the case defines a straight portion followed by a curved portion at substantially 90 degrees relative to the straight portion.

9. An illuminated optical laryngoscope comprising:
a case defining a tubular structure open at a first end; and
a main body comprising:
  a first straight segment,
  a curved second segment configured to follow a curvature of an interior of a mouth of a patient,
  at least one hinge formed in the second segment, and
  an optical system;
wherein the main body is configured to be inserted into the case;
wherein a portion of the case is curved and the curve of the second segment follows a curvature of the curved portion of the case; and
wherein the case defines a straight portion followed by the curved portion at substantially 90 degrees relative to the straight portion.

* * * * *